United States Patent [19]

Kemp et al.

[11] Patent Number: 4,884,447

[45] Date of Patent: Dec. 5, 1989

[54] HEARING FACULTY TESTING

[76] Inventors: David T. Kemp, 15 Burleigh Mead, Hatfield, Hertfordshire AL9 5ED; Peter Bray, 2 Ingleside, Mill Lane, Hookwood, Horley, Surrey RH6 0HX, both of England

[21] Appl. No.: 202,320

[22] Filed: Jun. 6, 1988

[30] Foreign Application Priority Data

Jun. 4, 1987 [GB] United Kingdom ............... 8713116

[51] Int. Cl.$^4$ .............................................. A61B 5/04
[52] U.S. Cl. ...................................... 73/585; 128/746
[58] Field of Search ........................... 73/585; 128/746

[56] References Cited

U.S. PATENT DOCUMENTS 3,799,146  3/1974  John et al. ........................... 128/746
4,374,526  2/1983  Kemp .

OTHER PUBLICATIONS

Acousting Emission Cochleography–Practical Aspects, D. T. Kemp, P. Bray, L. Alexander and A. M. Brown, From the Department of Audiology, Institute of Larynogology and Otology, Gray's Inn Road, London WCIX 8EE, England pp. 71–95.

Primary Examiner—John Chapman
Assistant Examiner—Michele Simons
Attorney, Agent, or Firm—Cushman, Darby & Cushman

[57] ABSTRACT

Hearing faculty test apparatus, for use in relation to the inner ear by way of the so-called cochlear echo, repeatedly applied a linearly balanced set of acoustic stimuli to the ear, individually sums each related set of responses to the stimuli set, interrogates each sum to detect components above a predetermined threshold, and averages sums on a selective basis depend on the interrogation. Preferably sums are passed for averaging only when wholly within the threshold. Also, averaging is preferably by use of two like averagers to which accepted sums are applied in alternating manner, with the two averages being fed to a correlator.

4 Claims, 1 Drawing Sheet

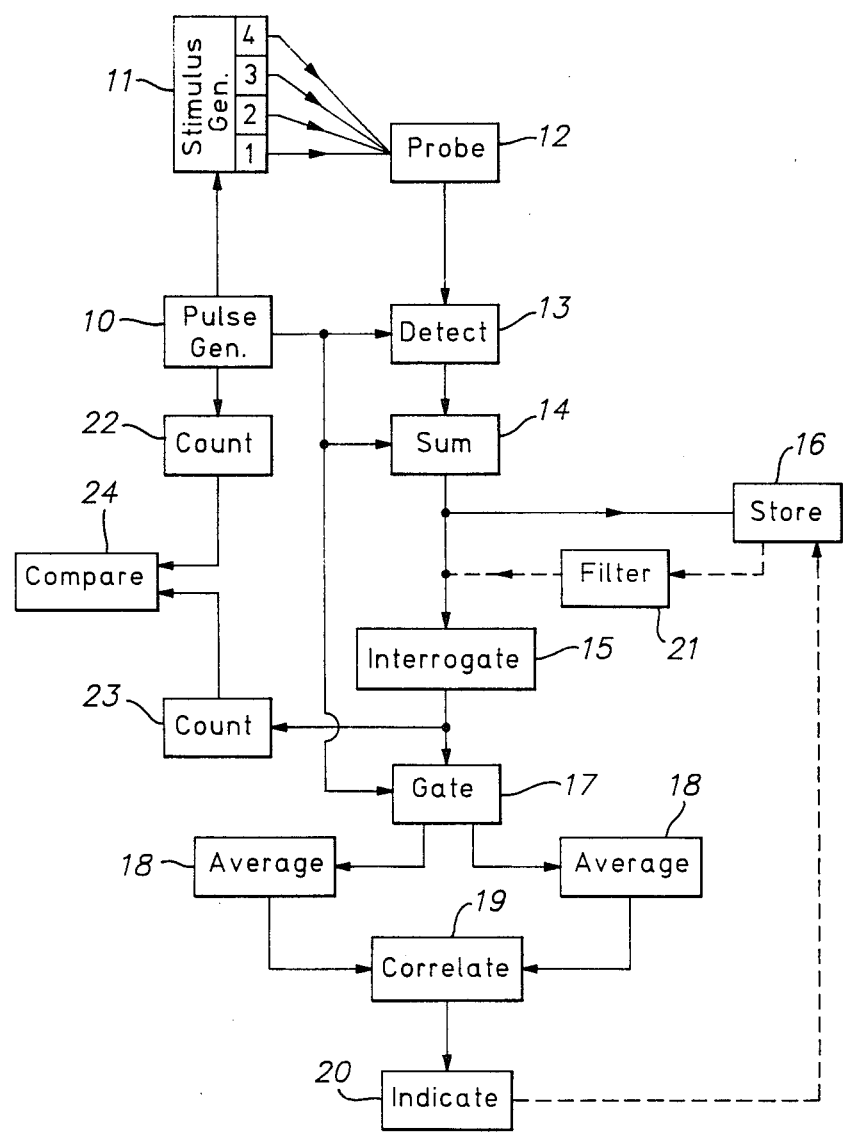

HEARING FACULTY TESTING

This invention concerns hearing faculty testing and more particularly that related to the inner ear by way of the so-called cochlear echo test as described in European Pat. No. 0015258 and corresponding U.S. Pat. No. 4374526.

The basis for this test is the finding that application of a sound stimulus to a patient's ear gives rise not only to a primary response involving reflection from the ear canal and middle ear, but also from the cochlea, and that this secondary response or echo is representative of the condition of the inner ear. A benefit of the test is that it can give an objective result, which contrasts with the subjective nature of any comparable prior technique. This benefit is of particular relevance when the subject is an infant or child.

However, as is commonly the case with most proposals for diagnostic techniques involving the generation of signals representing physiological functions, practical deployment can be subject to difficulty caused by the association of undesirable artifact components and noise with the signal of interest. The cochlear echo test is no exception.

Undesirable elements arise in several ways in this case. One element arises from the fact that, although in general terms the echo is delayed relative to the primary response there can be an overlap and, even though the response has decayed by the time the overlap occurs, the initial part of the echo can be significantly compromised in terms of straightforward detection. An element of noise occurs, as may be expected, from the test instrumentation itself. Other elements of noise are patient generated.

Proposals for resolution of this situation have been made in a paper entitled "Acoustic Emission Cochleography—Practical Aspects" by Kemp, Bray, Alexander and Brown, presented at the International Symposium on Cochlear Mechanics and Otoacoustic Emissions, Rome, Italy, Nov. 9–11, 1985 and thereafter published in Scand. Audiol. Suppl. 25, 71–95, 1986.

One measure of these proposals involves the application of a sequence of stimuli in what can be termed a linearly balanced set, with the related set of echoes being algebraically summed. The basis for this measure is that a primary response is linearly related to its stimulus whereas the echo is not, so that appropriate choice of stimuli levels and phases in a set can be such that summing of the related outputs allows effective elimination of the primary response.

Noise resulting from the instrumentation can be reduced to an acceptable level by repetitive testing and synchronous averaging of the outputs.

Patient induced noise falls into two categories: low level noise, particularly of a regular nature, such as caused by respiration, and high level noise of a random nature due to swallowing, grinding of teeth and other patient actions. This last noise was thought to be more problematical and the above proposals suggest that its occurrence be dealt with by rejection, prior to summation and averaging, of those sets of outputs containing components above the expected echo level of about 35 dB SPL, say. Because these outputs include components of at least comparable level during an initial period of at least 5 ms, say, from primary response overlap, it is important that such rejection be based on detection effected only over the remaining period of each signal output.

While these proposals improve the situation for some purposes, they are not found to be satisfactory in circumstances where an undue incidence of patient noise occurs because this will clearly be associated with excessive output rejection. Moreover the results can be unsatisfactory even when an adequate number of outputs are indicated as acceptable relative to the rejection threshold. One reason for this is that the initial period of the primary response varies from patient to patient and this is taken into account in operation of the prior proposals by setting the rejection threshold at a higher than ideal level during the remainder of the outputs. In the result output signals which are accepted and summed can still be subject to significant noise degradation. This is particularly important from a clinical point of view because persistent patient-induced noise is more frequently met when the patient is an infant or child.

An object of the present invention is to alleviate this last situation and, to this end, it is proposed that hearing faculty testing apparatus comprise means for repetitively applying to a patient's ear a linearly balanced sequential set of sound stimuli, means for detecting and producing a related set of electrical output signals representing the responses from said ear to said stimuli, means for individually summing each said set of output signals to produce a corresponding sum signal, means for interrogating each said sum signal to detect components above a predetermined threshold, and means for averaging said sum signals on a selective basis in response to said interrogation means.

This proposal is advantageous in that the entire response including both primary and cochlear elements is processed without need for any special prior measure to effect a degree of separation, interrogation is carried out over the complete cochlear response rather than a foreshortened representation of this response, and the predetermined threshold with reference to which the interrogation is conducted can now safely be set just above the expected maximum cochlear response level, suitably at about 40dB SPL without, as can otherwise be the case with the prior proposal, causing the rejection of useful output data due to the presence of a primary response of long duration.

Selection for the purposes of averaging is preferably effected on the basis of accepting sum signals which are wholly within the predetermined threshold.

Averaging is deployed, as indicated above, in order to increase the signal data of interest relative to remanent noise but it is appropriate, in practice, to provide some means for indicating when an acceptable result has been attained.

Preferably the sum signals accepted for averaging are applied in alternating manner to two averaging pools, with the averages form these pools being applied, in turn, to a correlator to provide an indication of the attainment of a useful result. In practice attainment of a useful result is indicated by the provision of a correlation factor not less than about 0.6 between the two pools.

It will be appreciated that, if the averaging is generally to be effective in attaining a useful result, a number of sum signals must be accepted and, in turn, a larger number of sets of stimuli will be applied to the patient with some of the related sum signals then being rejected. However, it is not practicable to continue in an open-ended manner until sufficient sum signals are accepted to provide an acceptable result, because the overall duration of any one test sequence must be compatible with the nature of the patient.

In practice the application of stimulus sets up to the order of 800 has generally been found possible in a single procedure and this should be adequate to produce a useful result with the great majority of patients. In fact recent practice in development of the invention has involved the application of as few as 80 sets, with about 200 being a typical number, in association with a useful result and with as few as 30% of the relevant sum signals being accepted.

It is appropriate, in case an acceptable result is not obtained by use of the procedure so far described, to afford the possibility for an alternative approach. For this purpose the sum signals are stored in their original form whereby further processing can be conducted. One alternative involves reprocessing the sum signals in the same manner again but with a higher threshold at the interrogation stage. Another alternative is to reprocess the sum signals with the original threshold again but after filtering with a view to reducing patient induced noise. For this last purpose narrow band pass filtering over a range of about 1-3 kHz is found to remove a large proportion of the noise and to allow assessment of the cochlear condition over its mid-frequency range.

For further clarification one embodiment of the invention as so far described is illustrated, by way of example, in schematic form in the accompanying drawing.

In the drawing, the output of a pulse generator 10 is applied to a stimulus generator 11 which produces a sequence of four sound stimuli, with three as compressional pulses and one as a rarefraction pulse, which stimuli form a linearly balanced set having a zero algebraic sum. These stimuli are successively applied to a patient's ear by way of a probe 12, which probe also conveys acoustic responses from the ear to a detector 13 where output signals are generated to represent these responses. These responses include both the primary and cochlear elements together with noise of one form or another. The detector can be synchronised with the pulse generator for the purposes of timing to identify individual responses in the sequence.

In any event the output signals from the detector are applied to a summing circuit 14 which acts to sum the signals related to each stimulus set, the circuit 14 also being synchronised with the pulse generator for timing purposes. The resultant sum signals are applied to an interrogation unit 15 and also to a store 16 where they are recorded for possible reprocessing.

The interrogation unit operates to pass on each sum signal wholly within a predetermined threshold normally set just above the maximum cochlear response level as mentioned above. Sum signals which are passed are applied in alternating sequence, under the control of a gate 17 responsive to the signals themselves and the pulse generator output, to one or the other of like signal averagers 18. Outputs from the averages are applied as inputs to a correlator 19, with the resultant correlation factor or some corresponding representation being presented at an indicator 20.

In the event that it does not prove possible to achieve a satisfactory result, as indicated by a correlation factor not less than 0.6 following application of a number of stimuli sets, reprocessing can be conducted in an alternative manner. This is indicated by a broken line connection from the indicator 20 to the store 16 and thence on to the interrogation unit 15, the stored sum signals being reprocessed with an increased threshold in unit 15 or with the same threshold following passage through a narrow pass filter 21.

Also, to the extent that it may not be appropriate to use any results derived on the basis of only a small number, or that additional data regarding the extent of a test procedure and its results is useful, additional facilities can be provided. Thus, respective counters 22 and 23 are shown connected for response to the pulse generator 10 and gate 17 to indicate the number of stimulus sets applied and the number of resultant response sum signals accepted for averaging, the counters being themselves connected to a comparator 24 to indicate the proportion of accepted sum signals to applied stimulus sets.

While the invention has been described with more particular reference to a specific form thereof as illustrated in the drawing, variation is possible within the scope of the appendant claims. For example, the sum signals need not be applied directly for interrogation but can be converted first to a frequency domain form. In another variation the sum signals can be interrogated in respect of sub-divided sections of each such signal, with sections being accepted for averaging on an individual basis. Again, averaging need not necessarily be conducted in two pools, but instead a common averager can be employed with correlation effected between the current average and the immediately preceding average.

We claim:
1. Hearing faculty testing apparatus comprising:
means for repetitively applying to a patient's ear a linearly balanced sequential set of sound stimuli,
means for detecting and producing a related set of electrical output signals representing the responses from said ear to said stimuli,
means for individually summing each said set of output signals to produce a corresponding sum signal,
means for interrogating each said sum signal to detect components above a predetermined threshold, and
means for averaging said sum signals on a selective basis in response to said interrogation means,
wherein said averaging means comprises two like averagers, and said interrogation means operates to apply said sum signals selected for averaging to said averagers in successive alternating manner.

2. Apparatus according to claim 1 comprising correlation means responsive to said two averagers to indicate the quality of averaging result.

3. Hearing faculty testing apparatus comprising:
means for repetitively applying to a patient's ear a linearly balanced sequential set of sound stimuli,
means for detecting and producing a related set of electrical output signals representing the responses from said ear to said stimuli,
means for individually summing each said set of output signals to produce a corresponding sum signal,
means for interrogating each said sum signal to detect components above a predetermined threshold,
means for averaging said sum signals on a selective basis in response to said interrogation means,
storage means for recording said sum signals, and
a narrow pass filter,
said storage means being operable to apply said recorded sum signals to said interrogation means by way of said filter to reprocess such signals in the event that an initial processing is unsatisfactory.

4. Hearing faculty testing apparatus comprising:

means for applying to a patient's ear a linearly balanced sequential set of sound stimuli;

means for detecting and producing related sets of electrical output signals representing the responses from said ear to said stimuli;

means for individually summing each said set of output signals to produce a corresponding sum signal;

means for interrogating each said sum signal to detect components above a predetermined threshold, such means being operable to pass only those of said sum signals wholly within said threshold;

two like means for averaging such means being respectively responsive in alternating manner to successive ones of said sum signals passed by said interrogating means; and correlation means responsive to said two averaging means.

* * * * *